United States Patent [19]

Fischer et al.

[11] Patent Number: 4,536,511

[45] Date of Patent: Aug. 20, 1985

[54] MEDICAMENTS CONTAINING MUZOLIMINE, THEIR USE AND PROCESSES FOR THEIR PRODUCTION

[75] Inventors: Wolfgang Fischer, Bergisch-Gladbach; Felix Leiblein, Cologne, both of Fed. Rep. of Germany

[73] Assignee: Bayer Aktiengesellschaft, Leverkusen, Fed. Rep. of Germany

[21] Appl. No.: 577,447

[22] Filed: Feb. 6, 1984

[30] Foreign Application Priority Data

Feb. 24, 1983 [DE] Fed. Rep. of Germany ....... 3306366

[51] Int. Cl.³ ............................................ A61K 31/415
[52] U.S. Cl. .................................. 514/404; 514/869; 514/960
[58] Field of Search ..................................... 424/273 P

[56] References Cited

U.S. PATENT DOCUMENTS 3,957,814  5/1976  Möller et al. .................... 424/273 P

FOREIGN PATENT DOCUMENTS 2319280  11/1974  Fed. Rep. of Germany ... 424/273 P

OTHER PUBLICATIONS

"Remington's Pharmaceutical Sciences", Mack Publishing Co. (Easton, Pa.), pp. 1553–1557, 1560–1563 and 1573, (1980).

Primary Examiner—Albert T. Meyers
Assistant Examiner—Joyce L. Morrison
Attorney, Agent, or Firm—Sprung Horn Kramer & Woods

[57] ABSTRACT

A storage-stable highly active muzolimine composition comprising by weight about
(a) 100 parts of muzolimine
(b) 40–500 parts of starch
(c) 20–100 parts of cellulose
(d) 0.2–5 parts of silica, and
(e) 0.1–3 parts of stearic acid, Ca stearate, Mg stearate and/or talc.

8 Claims, No Drawings

MEDICAMENTS CONTAINING MUZOLIMINE, THEIR USE AND PROCESSES FOR THEIR PRODUCTION

The present invention relates to an improved solid medicament formulation of the active compound muzolimine[3-amino-1-(α-methyl-3,4-dichlorobenzyl)-5-pyrazolone], processes for its production and the use of the medicament as a diuretic, saluretic, antithrombotic and antihypertensive agent.

Muzolimine and 3-amino-5-pyrazolones of similar structure and their pharmacological effects are disclosed in DE-OS (German Published Specification) 2,319,280. A formulation for 3-amino-5-pyrazolones is also described in this reference, according to which 200 g of the active compound are milled to a powder, mixed with 300 g of lactose and 200 g of potato starch and, after moistening with an aqueous gelatine solution, are granulated through a screen. After drying, 60 g of talc and 5 g of sodium lauryl sulphate are added. About 10,000 tablets, each containing 20 mg of active compound, are compressed from this mixture.

However, the medicaments thus produced have a number of disadvantages, in particular their storage stability is low (brown discolorations are produced on the tablets after only a few months) and their release of active compound is inadequate. Thus the object of the invention was to produce a solid formulation for muzolimine which is free of the disadvantages mentioned and is simple to produce by industrial processes. This object is achieved according to the invention by a formulation which contains (a) 100 parts by weight of muzolimine,
(b) 40–500 parts by weight of starch,
(c) 20–100 parts by weight of cellulose,
(d) 0.2–5 parts by weight of silica, and
(e) 0.1–3 parts by weight of stearic acid, Ca stearate, Mg stearate and/or talc.

In the formulations according to the invention, the ratio of the weight of muzolimine to the total weight of the additives is preferably 1:0.8 to 1:10, particularly preferably 1:1 to 1:4.

The preparations according to the invention are particularly suitable for the production of granules which can be compressed to form tablets or filled into capsules. It is possible for the tablets to be used either uncoated or coated in a manner known per se (see, for example, Sucker, Fuchs and Speiser: Pharmazeutische Technologie (Pharmaceutical Technology), Georg Thieme, Stuttgart).

The active compound muzolimine is obtained by (A) reacting, optionally in the presence of inert solvents and basic or acid catalysts, such as alkali metal and alkaline earth metal hydroxides and carbonates, or such as hydrogen halide acids, sulphuric acid or sulphonic acids, at temperatures between 10° and 200° C., a hydrazine of the formula

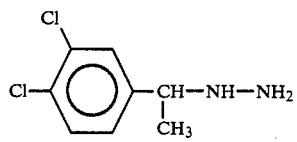

with acetic acid derivatives, which can, where appropriate, occur in various tautomeric forms, of the general formula

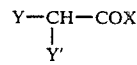

in which
X represents a hydroxyl, alkoxy, aralkoxy, amino or alkylamino radical,
Y represents hydrogen and
Y' represents nitrile, or
Y and Y' together represent the group

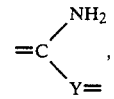

Y" representing an alkoxy, aryloxy, aralkoxy, alkylmercapto or alkylmercapto radical or the amino group, or (B) reacting, optionally in the presence of inert solvents and inorganic or organic bases, such as alkali metal hydroxides, carbonates, alcoholates, hydrides or amides, at temperatures between 10° and 200° C., compounds of the general formula VIII

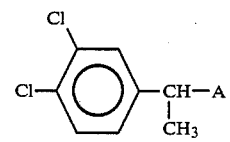

in which
A represents a leaving group, such as halogen or the dialkyloxonium, dialkylsulphonium or trialkylammonium radical or the arylsulphonyl or trifluoromethylsulphonyl radical,
with 3-amino-5-pyrazolone of the formula

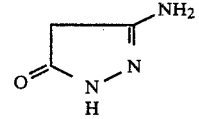

or (C) reacting, optionally in the presence of inert solvents, at temperatures between 50° and 150° C., preferably under elevated pressure, a 5-pyrazolone derivative of the general formula

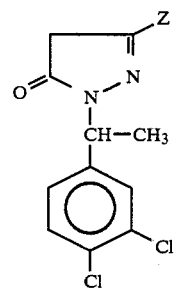

in which

Z represents Cl or Br, with ammonia.

In the formulations according to the invention, muzolimine is employed in the form of a finely divided powder, preferably as the hemihydrate.

The preparations according to the invention contain, as component (b), starch, some of which (about 10–30% by weight of the total amount of starch) is optionally in a preagglutinated form, in an amount which corresponds to 0.4 to 5 times, preferably 0.6 to 2.5 times, the weight of the active compound (muzolimine). Examples of suitable starches are those from potatoes, wheat, corn or rice, preferably corn.

Component (c) of the formulations according to the invention is cellulose (preferably microcrystalline or powdered; the microcrystalline type is particularly preferred) in 0.2 to 1 times, preferably 0.3 to 0.7 times, the amount of the active compound.

Silicas, preferably colloidal silicon dioxide, are used as component (d) of the formulations according to the invention. The amount of component (d) is 0.2–5 parts by weight, preferably 0.25–0.5 part by weight, relative to 100 parts of active compound.

The preparations according to the invention contain, as a further additive, 0.1–3 parts by weight, preferably 0.2–1.5 parts by weight, relative to 100 parts by weight of muzolimine, of magnesium stearate, calcium stearate, stearic acid and/or talc, preferably magnesium stearate.

In processing the preparations according to the invention to form granules, the selected industrial process can be either dry or moist granulation, preferably moist granulation. This process can be carried out in a mixing granulator or by the procedure of fluidized bed granulation, mixing granulation being preferred.

The granulating auxiliaries which can be used are starch pastes, preagglutinated starch and/or polyvinylpyrrolidone (preferred molecular weight 15,000–60,000). Starch pastes and/or preagglutinated starch (especially corn starch) are preferably used.

In the production of the medicament according to the invention, the procedure is preferably such that, in a first step, components (a), (c) and (d) and a portion (preferably 50–95% by weight) of component (b) are mixed, granulated dry or moist (in the latter case, the portion of component (b) preferably contains the starch paste or the preagglutinated starch, and in the former case, preferably 50–70% of component (e) are added), the granules are screened, mixed with the remainder of component (b) and component (e), and the mixture is compressed to form tablets or filled into capsules in a manner known per se.

The absolute amount by weight of the active compound contained in the medicaments according to the invention depends on their therapeutic use. Single doses of 20 mg, 30 mg and 240 mg of the (anhydrous) active compound per capsule or tablet are particularly preferred.

The exemplary embodiments which follow relate to medicament preparations which are particularly preferred according to the invention. The formulations are stable on storage for at least 5 years and, using the release model of USP XX, they release the active compound virtually completely in 2 hours.

EXAMPLE 1

20 kg of muzolimine are mixed with 33 kg of corn starch, 0.6 kg of colloidal silicon dioxide, 14 kg of microcrystalline cellulose and 6 kg of preagglutinated corn starch, and after the addition of water, are granulated in a mixing granulator of type MGT supplied by Lödige, Paderborn (F.R.G.). The granules are then dried by passing warm air into a fluidized bed in equipment of type WST supplied by Glatt AG, Binzen/Lörrach (F.R.G.) up to a product temperature of 45°–55° C. The material is screened, mixed with 6 kg of starch and 0.4 kg of Mg stearate and compressed to form tablets weighing 80 mg, or 80 mg are filled into capsules.

It is also possible to process the above mixture by the procedure of Example 2 which follows.

EXAMPLE 2

240 kg of muzolimine are mixed with 156.5 kg of corn starch, 90 kg of microcrystalline cellulose, 1 kg of colloidal silicon dioxide and 1.5 kg of Mg stearate. The mixture is compacted dry in a roller mill supplied by Alexander, Remscheid (F.R.G.).

After crushing and screening, the granules thus obtained are mixed with 10 kg of starch and 1 kg of Mg stearate, and compressed to form tablets, weighing 500 mg, or 500 mg are filled into capsules. The above mixture can, of course, also be processed by the procedure in Example 1.

It will be appreciated that the instant specification and examples are set forth by way of illustration and not limitation, and that various modifications and changes may be made without departing from the spirit and scope of the present invention.

What is claimed is:

1. A muzolimine-containing composition in the form of a compressed tablet and comprising by weight about
   (a) 100 parts of muzolimine
   (b) 40–500 parts of starch
   (c) 20–100 parts of microcrystalline cellulose
   (d) 0.2–5 parts of colloidal silica, and
   (e) 0.1–3 parts of at least one of stearic acid, Ca stearate, Mg stearate and talc.

2. A composition according to claim 1, comprising by weight about
   100 parts of component (a)
   60–250 parts of component (b)
   30–70 parts of component (c)
   0.25–0.5 parts of component (d), and
   0.2–1.5 parts of component (e).

3. A composition according to claim 1, wherein component (b) comprises corn starch of which part may be in an agglutinated form.

4. A composition according to claim 1, wherein component (e) comprises Mg stearate.

5. A composition according to claim 1, in the form of a unit dose containing about 20, 30 or 240 mg of muzolimine.

6. In the administration of muzolimine to a patient in tablet form, the improvement which comprises administering tablets formed of the composition according to claim 1.

7. A process for the production of a composition according to claim 1, comprising mixing components (a), (c), (d), 50–95% by weight of component (b) and 50–70% by weight of component (e), dry granulating the mixture, screening the granules, mixing the granules with the remainder of components (b) and (e) and compressing the mixture of form tablets.

8. A process for the production of the composition according to claim 1, comprising mixing components (a), (c), (d) and 50–95% by weight of component (b), moist granulating the mixture, screening the granules, mixing the granules with the remainder of component (b) and component (e) and compressing the mixture to form tablets.

* * * * *